United States Patent
Xie

(10) Patent No.: US 9,708,193 B2
(45) Date of Patent: Jul. 18, 2017

(54) SYNTHESIS OF ALUMINOSILICATE LEV FRAMEWORK TYPE ZEOLITES

(71) Applicant: Chevron U.S.A. Inc., San Ramon, CA (US)

(72) Inventor: Dan Xie, Richmond, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 170 days.

(21) Appl. No.: 14/871,174

(22) Filed: Sep. 30, 2015

(65) Prior Publication Data

US 2017/0050857 A1   Feb. 23, 2017

Related U.S. Application Data

(60) Provisional application No. 62/207,454, filed on Aug. 20, 2015.

(51) Int. Cl.
*C01B 39/04* (2006.01)
*C01B 39/48* (2006.01)
*C01B 39/02* (2006.01)

(52) U.S. Cl.
CPC .............. *C01B 39/48* (2013.01); *C01B 39/04* (2013.01); *C01B 39/026* (2013.01)

(58) Field of Classification Search
CPC ........... B01J 29/70; C01B 39/48; C01B 39/04
See application file for complete search history.

(56) References Cited

U.S. PATENT DOCUMENTS

| | | | | |
|---|---|---|---|---|
| 3,314,752 A | * | 4/1967 | Kerr | ............... C01B 33/2876 423/705 |
| 3,459,676 A | * | 8/1969 | Kerr | ...................... C01B 39/48 423/705 |
| 3,692,470 A | | 9/1972 | Ciric | |
| 4,061,717 A | * | 12/1977 | Kerr | ...................... B01J 29/06 423/702 |
| 4,372,930 A | | 2/1983 | Short et al. | |
| 4,508,837 A | * | 4/1985 | Zones | ..................... B01J 29/04 423/326 |
| 5,693,215 A | * | 12/1997 | Zones | ..................... B01J 29/04 208/111.01 |
| 6,004,527 A | * | 12/1999 | Murrell | ................. B01J 29/035 423/328.2 |
| 6,350,429 B1 | * | 2/2002 | Murrell | ................. B01J 29/035 423/305 |
| 9,156,706 B2 | | 10/2015 | Davis | |
| 9,573,819 B2 | * | 2/2017 | Xie | ........................ C01B 39/48 |
| 9,598,282 B2 | * | 3/2017 | Han | ...................... B82Y 15/00 |
| 2016/0114313 A1 | * | 4/2016 | Xie | .................. B01D 53/9445 423/213.2 |
| 2016/0115037 A1 | * | 4/2016 | Xie | ........................ C01B 39/48 423/718 |
| 2016/0115038 A1 | * | 4/2016 | Xie | ........................ C01B 39/48 423/704 |

FOREIGN PATENT DOCUMENTS

| | | |
|---|---|---|
| EP | 0091048 | 10/1983 |
| WO | 2016003503 | 1/2016 |
| WO | 2016064451 | 4/2016 |

OTHER PUBLICATIONS

International Search Report, International Appl. No. PCT/US2016/034236, mailed Aug. 24, 2016.

T. Inoue, M. Itakura, H. Jon, Y. Oumi, A. Takahashi, T. Fujitani and T. Sano "Synthesis of LEV zeolite by interzeolite conversion method and its catalytic performance in ethanol to olefins reaction" Micropor. Mesopor. Mater. 2009, 122, 149-154.

B. Han, S-H. Lee, C-H. Shin, P.A. Cox and S.K. Hong "Zeolite Synthesis Using Flexible Diquaternary Alkylammonium Ions $(C_nH_{2n+1})_2HN^+(CH_2)_5N^+H(C_nH_{2n+1})_2$ with n=1-5 as Structure-Directing Agents" Chem. Mater. 2005, 17, 477-486.

K. Yamamoto, T. Ikeda, M. Onodera, A. Muramatsu, F. Mizukami, Y. Wang and H. Gies "Synthesis and structure analysis of RUB-50, an LEV-type aluminosilicate zeolite" Microporous Mesoporous Mater.128, 150-157, 2010.

\* cited by examiner

*Primary Examiner* — David M Brunsman
(74) *Attorney, Agent, or Firm* — Terrence M. Flaherty

(57) ABSTRACT

A method is disclosed for making LEV framework type zeolites using N,N'-dimethyl-1,4-diazabicyclo[2.2.2]octane dications as a structure directing agent.

4 Claims, 2 Drawing Sheets

SYNTHESIS OF ALUMINOSILICATE LEV FRAMEWORK TYPE ZEOLITES

CROSS-REFERENCE TO RELATED APPLICATIONS

This application claims the priority benefit of U.S. Provisional Application No. 62/207,454, filed Aug. 20, 2015, which is incorporated herein by reference.

TECHNICAL FIELD

This disclosure relates generally to a method for preparing LEV framework type zeolites using N,N'-dimethyl-1,4-diazabicyclo[2.2.2]octane dications as a structure directing agent.

BACKGROUND

Molecular sieves are classified by the Structure Commission of the International Zeolite Association according to the rules of the IUPAC Commission on Zeolite Nomenclature. According to this classification, framework type zeolites and other crystalline microporous molecular sieves, for which a structure has been established, are assigned a three letter code and are described in the "*Atlas of Zeolite Framework Types*," Sixth Revised Edition, Elsevier, 2007.

One known molecular sieve for which a structure has been established is the material designated as LEV, which is a molecular sieve characterized by heptadecahedral cavities to which LEV framework type materials owe their large micropore volume (about 0.3 cm$^3$/g), although this structure only has small eight-membered ring (8MR) pore openings. Due to its unique structure, LEV framework type zeolites are of significant interest as catalysts for methanol-to-olefins (MTO) conversion and NO reduction. Examples of LEV framework type materials include levyne, AlPO-35, CoDAF-4, LZ-132, NU-3, RUB-1, SAPO-35, ZK-20, and ZnAPO-35.

Synthetic LEV framework zeolites are typically prepared using exotic organotemplates as structure directing agents, such as quinuclidine-based templates. The commercial development of LEV framework type zeolites has been hindered by the complexity of the structure directing agent required for its synthesis and hence there is significant interest in finding alternative structure directing agents for the synthesis of aluminosilicate LEV framework type zeolites, particularly materials with SiO$_2$/Al$_2$O$_3$ mole ratios that are suitable for MTO conversion and NO$_x$ reduction applications.

It has now been found that LEV framework type zeolites having SiO$_2$/Al$_2$O$_3$ mole ratios ranging from 10 to 55 can be prepared using N,N'-dimethyl-1,4-diazabicyclo[2.2.2]octane dications as a structure directing agent. This cationic species can be produced conveniently and inexpensively from commercially available raw materials.

SUMMARY

In one aspect, there is provided a method of preparing LEV framework type zeolite by contacting under crystallization conditions (1) at least one source of silicon oxide; (2) at least one source of aluminum oxide; (3) at least one source of an element selected from Groups 1 and 2 of the Periodic Table; (4) N,N'-dimethyl-1,4-diazabicyclo[2.2.2]octane dications; and (5) hydroxide ions.

In another aspect, there is provided a process for preparing an LEV framework type zeolite by: (a) preparing a reaction mixture containing: (1) at least one source of silicon oxide; (2) at least one source of aluminum oxide; (3) at least one source of an element selected from Groups 1 and 2 of the Periodic Table; (4) N,N'-dimethyl-1,4-diazabicyclo[2.2.2]octane dications; (5) hydroxide ions; and (6) water; and (b) subjecting the reaction mixture to crystallization conditions sufficient to form crystals of the LEV framework type zeolite.

In one aspect, there is provided an aluminosilicate LEV framework type zeolite containing N,N'-dimethyl-1,4-diazabicyclo[2.2.2]octane dications within its pore structure.

In another aspect, there is also provided a crystalline LEV framework type zeolite having a composition, as-synthesized and in the anhydrous state, in terms of mole ratios, as follows:

|  | Broad | Exemplary |
| --- | --- | --- |
| SiO$_2$/Al$_2$O$_3$ | 10 to 55 | 15 to 40 |
| Q/SiO$_2$ | 0.02 to 0.20 | 0.05 to 0.20 |
| M/SiO$_2$ | 0.01 to 0.20 | 0.02 to 0.15 | wherein Q represents N,N'-dimethyl-1,4-diazabicyclo[2.2.2] octane dications and M is selected from the group consisting of elements from Groups 1 and 2 of the Periodic Table.

DETAILED DESCRIPTION

Figure 1:
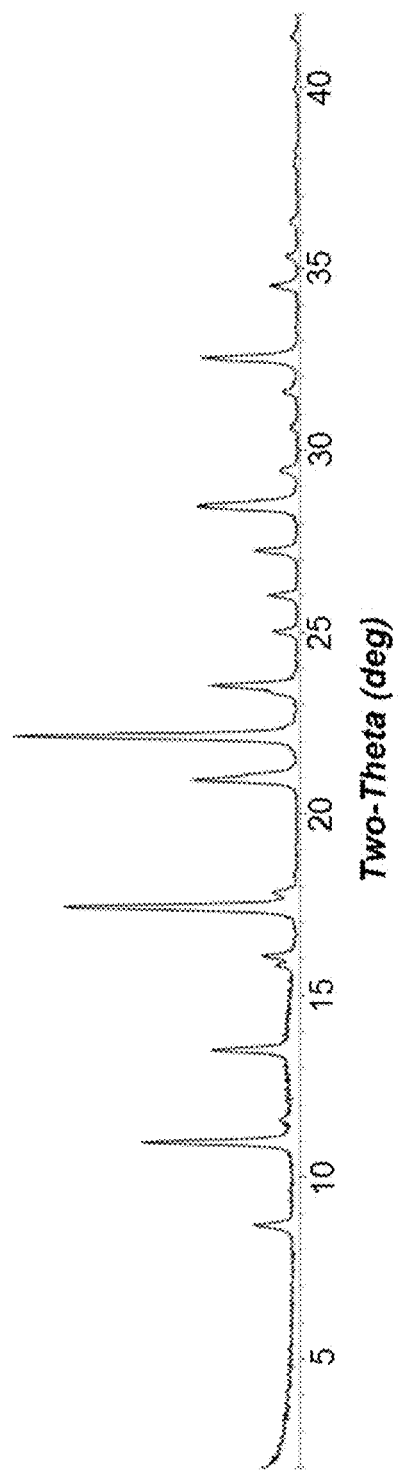
FIG. 1 is a powder X-ray diffraction (XRD) pattern of the as-synthesized zeolite prepared in Example 1.

The following terms will be used throughout the specification and will have the following meanings unless otherwise indicated.

The term "zeolite" refers to crystalline aluminosilicate compositions which are microporous and which are formed from corner-sharing AlO$_2$ and SiO$_2$ tetrahedra.

The term "framework type" is used in the sense described in the "*Atlas of Zeolite Framework Types*," Sixth Revised Edition, Elsevier, 2007.

As used herein, the numbering scheme for the Periodic Table Groups is as disclosed in *Chem. Eng. News*, 63(5), 26-27 (1985).

In preparing LEV framework type zeolites, an N,N'-dimethyl-1,4-diazabicyclo[2.2.2]octane dication is used as a structure directing agent ("SDA"), also known as a crystallization template. The SDA useful for making LEV framework type zeolites is represented by the following structure (1):

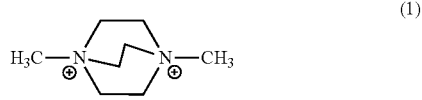

N,N'-dimethyl-1,4-diazabicyclo[2.2.2]octane dication

The SDA cation is associated with anions which can be any anion that is not detrimental to the formation of the zeolite. Representative anions include elements from Group 17 of the Periodic Table (e.g., fluoride, chloride, bromide, and iodide), hydroxide, sulfate, tetrafluoroborate, acetate, carboxylate, and the like.

Reaction Mixture

In general, the aluminosilicate LEV framework type zeolite is prepared by: (a) preparing a reaction mixture containing (1) at least one source of silicon oxide; (2) at least one source of aluminum oxide; (3) at least one source of an element selected from Groups 1 and 2 of the Periodic Table; (4) N,N'-dimethyl-1,4-diazabicyclo[2.2.2]octane dications; (5) hydroxide ions; and (6) water; and (b) subjecting the reaction mixture to crystallization conditions sufficient to form crystals of the LEV framework type zeolite.

The composition of the reaction mixture from which the zeolite is formed, in terms of mole ratios, is identified in Table 1 below:

TABLE 1

|  | Broad | Exemplary |
| --- | --- | --- |
| $SiO_2/Al_2O_3$ | 10 to 100 | 15 to 60 |
| $M/SiO_2$ | 0.05 to 0.80 | 0.10 to 0.45 |
| $Q/SiO_2$ | 0.10 to 0.80 | 0.15 to 0.30 |
| $OH/SiO_2$ | 0.20 to 1.00 | 0.20 to 0.60 |
| $H_2O/SiO_2$ | 10 to 50 | 15 to 50 | wherein compositional variables M and Q are as described herein above.

Sources useful herein for silicon oxide include fumed silica, precipitated silicates, silica hydrogel, silicic acid, colloidal silica, tetra-alkyl orthosilicates (e.g., tetraethyl orthosilicate), and silica hydroxides.

Sources useful herein for aluminum oxide include aluminates, alumina, and aluminum compounds (e.g., aluminum chloride, aluminum hydroxide, and aluminum sulfate), kaolin clays, and other zeolites (e.g., zeolite Y).

As described herein above, for each embodiment described herein, the reaction mixture can be formed using at least one source of an element selected from Groups 1 and 2 of the Periodic Table (referred to herein as M). In one sub-embodiment, the reaction mixture is formed using a source of an element from Group 1 of the Periodic Table. In another sub-embodiment, the reaction mixture is formed using a source of sodium (Na). Any M-containing compound which is not detrimental to the crystallization process is suitable. Sources for such Groups 1 and 2 elements include oxides, hydroxides, nitrates, sulfates, halides, acetates, oxalates and citrates thereof.

Optionally, the reaction mixture may contain seed crystals. In one embodiment, synthesis of the crystalline zeolite is facilitated by the presence of 0.05 to 10.0 wt. % (e.g., from 1 to 5 wt. %) seed crystals based on the total weight of the reaction mixture. The seed crystals can be isostructural with the desired zeolite, for example, the product of a previous synthesis.

For each embodiment described herein, the reaction mixture can be supplied by more than one source. Also, two or more reaction components can be provided by one source.

The reaction mixture can be prepared either batch wise or continuously. Crystal size, morphology and crystallization time of the crystalline zeolite described herein can vary with the nature of the reaction mixture and the crystallization conditions.

Crystallization and Post-Synthesis Treatment

Crystallization of the LEV framework type zeolite described herein can be carried out under either static, tumbled or stirred conditions in a suitable reactor vessel, such as for example polypropylene jars or Teflon-lined or stainless steel autoclaves, at a temperature of from 125° C. to 200° C. for a time sufficient for crystallization to occur at the temperature used, e.g., from 1 day to 28 days.

Once the zeolite crystals have formed, the solid product is separated from the reaction mixture by standard mechanical separation techniques such as centrifugation or filtration. The crystals are water-washed and then dried to obtain the as-synthesized zeolite crystals. The drying step is typically performed at a temperature of less than 200° C.

As a result of the crystallization process, the recovered crystalline zeolite product contains within its pore structure at least a portion of the structure directing agent used in the synthesis.

The structure directing agent is typically at least partially removed from the zeolite by calcination before use. Calcination consists essentially of heating the zeolite comprising the structure directing agent at a temperature of from 200° C. to 800° C. in the presence of an oxygen-containing gas, optionally in the presence of steam. The structure directing agent can also be removed by photolysis techniques as described in U.S. Pat. No. 6,960,327.

To the extent desired and depending on the composition of the zeolite, any cations in the as-synthesized or calcined zeolite can be replaced in accordance with techniques well known in the art by ion exchange with other cations. Preferred replacing cations include metal ions, hydrogen ions, hydrogen precursor, e.g., ammonium ions and mixtures thereof. Particularly preferred cations are those which tailor the catalytic activity for certain hydrocarbon conversion reactions. These include hydrogen, rare earth metals and metals of Groups 2 to 15 of the Periodic Table of the Elements. As used herein, the term "as-synthesized" refers to the zeolite in its form after crystallization, prior to removal of the SDA cation.

The zeolite disclosed herein can be formulated with into a catalyst composition by combination with other materials, such as binders and/or matrix materials, which provide additional hardness or catalytic activity to the finished catalyst.

Characterization of the Zeolite

The LEV framework type zeolites made by the process disclosed herein have a composition (in terms of mole ratios), as-synthesized and in the anhydrous state, as described in Table 2 below:

TABLE 2

|  | Broad | Exemplary |
| --- | --- | --- |
| $SiO_2/Al_2O_3$ | 10 to 55 | 15 to 40 |
| $Q/SiO_2$ | 0.02 to 0.20 | 0.05 to 0.20 |
| $M/SiO_2$ | 0.01 to 0.20 | 0.02 to 0.15 | wherein compositional variables Q and M are as described herein above.

It should be noted that the as-synthesized form of the LEV framework type zeolite may have molar ratios different from the molar ratios of reactants of the reaction mixture used to prepare the as-synthesized form. This result may occur due to incomplete incorporation of 100% of the reactants of the reaction mixture into the crystals formed (from the reaction mixture).

The LEV framework type zeolites synthesized by the process described herein are characterized by their X-ray diffraction pattern. X-ray diffraction patterns representative of LEV framework type zeolites can be referenced in the "Collection of Simulated XRD Powder Patterns for Zeolites," Fifth Revised Edition, Elsevier, 2007. Minor variations in the diffraction pattern can result from variations in the mole ratios of the framework species of the particular sample due to changes in lattice constants. In addition, sufficiently small crystals will affect the shape and intensity of peaks, leading to significant peak broadening. Minor variations in the diffraction pattern can result from variations in the organic compound used in the preparation. Calcination can also cause minor shifts in the X-ray diffraction pattern. Notwithstanding these minor pertubations, the basic crystal structure remains unchanged.

The powder X-ray diffraction patterns presented herein were collected by standard techniques. The radiation was $CuK_\alpha$ radiation. The peak heights and the positions, as a function of 2θ where θ is the Bragg angle, were read from the relative intensities of the peaks, and d, the interplanar spacing corresponding to the recorded lines, can be calculated.

EXAMPLES

The following illustrative examples are intended to be non-limiting.

Example 1

1.30 g of deionized water, 4.70 g of sodium silicate solution (Sigma-Aldrich) and 5.95 g of a 19% N,N'-dimethyl-1,4-diazabycyclo[2.2.2]octane hydroxide solution (SACHEM Inc.) were mixed together in a Teflon liner. Then, 1.00 g of LZ-210 Y-zeolite powder was added to the solution. The resulting gel was stirred until it became homogeneous. The liner was capped and placed within a Parr steel autoclave reactor. The autoclave was placed in an oven and heated at 135° C. for 4 days. The solid products were recovered from the cooled reactor by centrifugation, washed with deionized water and dried at 95° C.

Figure 2:
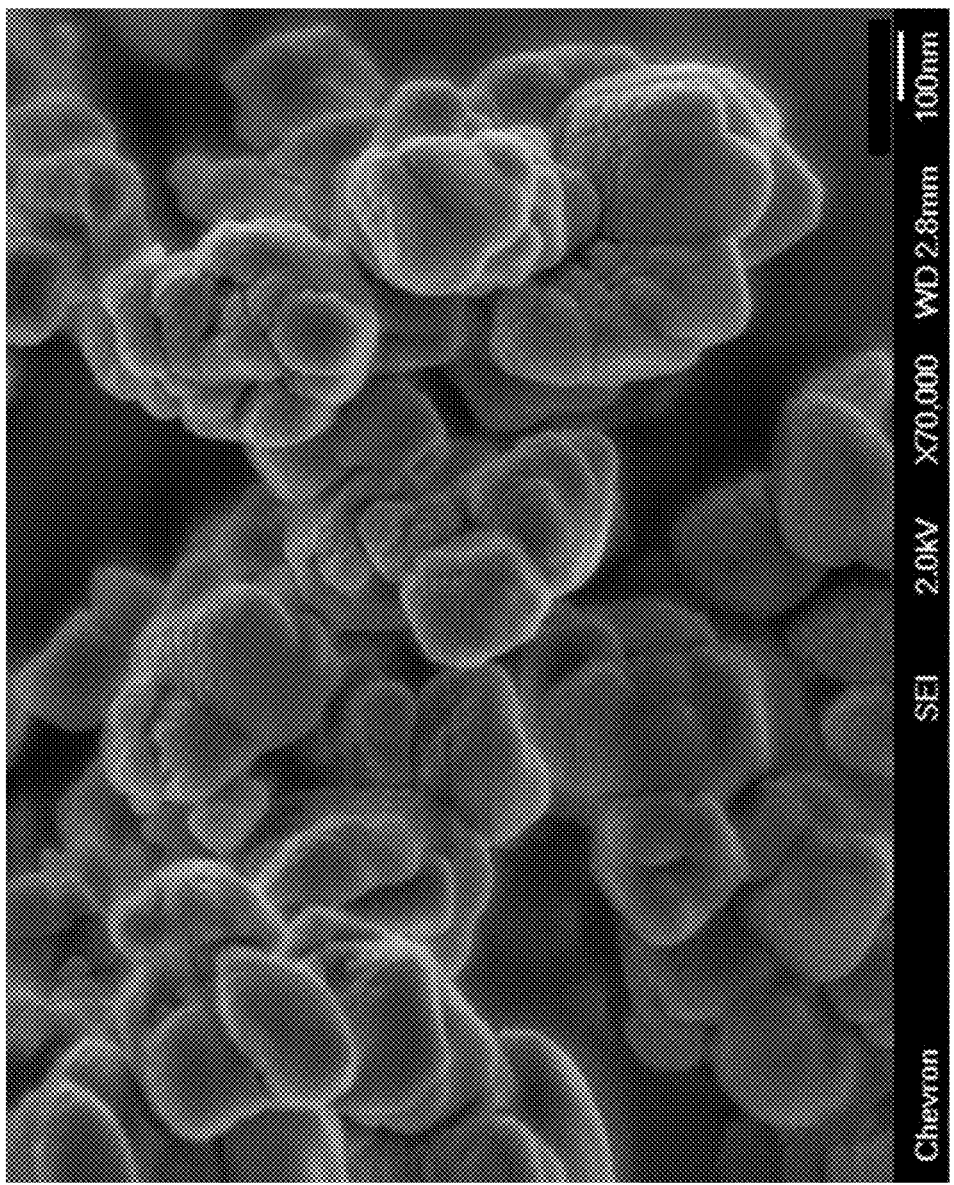
FIG. 2 is a scanning electron micrograph (SEM) image of the as-synthesized zeolite prepared in Example 1.

The resulting product was analyzed by powder XRD and SEM. The powder XRD pattern is shown in FIG. 1 and indicates that the material is a pure LEV framework type zeolite. The SEM image is shown in FIG. 2 and indicates a uniform field of crystals.

The product had a $SiO_2/Al_2O_3$ mole ratio of 14.6, as determined by ICP elemental analysis.

Example 2

4.03 g of deionized water, 19.32 g of sodium silicate solution (Sigma-Aldrich) and 22.33 g of a 19% N,N'-dimethyl-1,4-diazabycyclo[2.2.2]octane hydroxide solution (Sachem) were mixed together in a Teflon liner. Then, 3.00 g of LZ-210 Y-zeolite powder was added to the solution. The resulting gel was stirred until it became homogeneous. The liner was capped and placed within a Parr steel autoclave reactor. The autoclave was placed in an oven and heated at 150° C. for 3 days. The solid products were recovered from the cooled reactor by centrifugation, washed with deionized water and dried at 95° C.

The resulting product was identified by powder XRD and SEM to be pure LEV framework type zeolite.

The product had a $SiO_2/Al_2O_3$ mole ratio of 17.4, as determined by ICP elemental analysis.

Example 3

14.10 g of sodium silicate solution (Sigma-Aldrich) and 26.80 g of 19% N,N'-dimethyl-1,4-diazabycyclo[2.2.2]octane hydroxide solution (Sachem) were mixed together in a Teflon liner. Then, 3.00 g of CBV720 Y-zeolite powder (Zeolyst International, $SiO_2/Al_2O_3$ mole ratio=30) was added to the solution. The resulting gel was stirred until it became homogeneous. The liner was capped and placed within a Parr steel autoclave reactor. The autoclave was placed in an oven and heated at 150° C. for 3 days. The solid products were recovered from the cooled reactor by centrifugation, washed with deionized water and dried at 95° C.

The resulting product was identified by powder XRD and SEM to be pure LEV framework type zeolite.

The product had a $SiO_2/Al_2O_3$ mole ratio of 18.6, as determined by ICP elemental analysis.

Example 4

The as-synthesized zeolite product of Example 1 was calcined inside a muffle furnace under a flow of air heated to 540° C. at a rate of 1° C./minute and held at 540° C. for 5 hours, cooled and then analyzed by powder XRD. The powder XRD pattern indicated that the material remains stable after calcination to remove the organic SDA.

Example 5

The calcined product from Example 4 was subjected to a micropore volume analysis using $N_2$ as adsorbate and via the BET method. The zeolite exhibited a considerable void volume with a micropore volume of 0.25 $cm^3/g$.

Example 6

Methanol Conversion

Ammonium-exchanged product was pelletized at 5 kpsi, crushed and meshed to 20-40. 0.20 g of catalyst (diluted 4:1 v/v with alundum) was centered in a stainless steel downflow reactor in a split tube furnace. The catalyst was preheated in-situ under flowing nitrogen at 400° C. A feed of 10% methanol in nitrogen was introduced into the reactor at a rate of 1.3 $h^{-1}$ WHSV.

Reaction data was collected using a plug flow and an Agilent on-line gas chromatograph with an FID detector. Reaction products were analyzed at various time points on an HP-PLOT Q column. The results are summarized in Table 3.

TABLE 3

| Product | 0.4 Hour Data | 0.7 Hour Data | 1.1 Hour Data | 1.5 Hour Data |
|---|---|---|---|---|
| Conversion | 1.00 | 1.00 | 1.00 | 1.00 |
| Sum $C_1$-$C_3$ paraffins | 0.18 | 0.16 | 0.10 | 0.09 |
| Ethylene | 0.50 | 0.60 | 0.59 | 0.55 |
| Propylene | 0.20 | 0.18 | 0.15 | 0.13 |
| Summed Butanes/Butenes | 0.06 | 0.02 | 0.02 | 0.03 |
| Summed Pentanes/Pentenes | 0.06 | 0.03 | 0.13 | 0.21 |
| Ethylene/Propylene ratio | 2.49 | 3.35 | 3.86 | 4.28 |

The products shown in Table 3 are consistent with those for a small pore zeolite in terms of product shape-selectivity in the reaction of methanol being catalytically converted to olefins of mostly $C_2$-$C_4$ size. No aromatic products were observed.

As used herein, the term "comprising" means including elements or steps that are identified following that term, but any such elements or steps are not exhaustive, and an embodiment can include other elements or steps.

Unless otherwise specified, the recitation of a genus of elements, materials or other components, from which an individual component or mixture of components can be selected, is intended to include all possible sub-generic combinations of the listed components and mixtures thereof.

All documents cited in this application are herein incorporated by reference in their entirety to the extent such disclosure is not inconsistent with this text.

The invention claimed is:

1. A method of preparing an LEV framework type zeolite, comprising:
    (a) preparing a reaction mixture containing:
        (1) at least one source of silicon oxide;
        (2) at least one source of aluminum oxide;
        (3) at least one source of an element (M) selected from Groups 1 and 2 of the Periodic Table;
        (4) N,N'-dimethyl-1,4-diazabicyclo[2.2.2]octane dications (Q);
        (5) hydroxide ions; and
        (6) water; and
    (b) subjecting the reaction mixture to crystallization condition sufficient to form crystals of the zeolite, wherein the zeolite is prepared from a reaction comprising, in terms of mole ratios, the following:

| | |
|---|---|
| $SiO_2/Al_2O_3$ | 15 to 60 |
| $M/SiO_2$ | 0.10 to 0.45 |
| $Q/SiO_2$ | 0.15 to 0.30 |
| $OH/SiO_2$ | 0.20 to 0.60 |
| $H_2O/SiO_2$ | 15 to 30. |

2. The method of claim 1, wherein the zeolite has a composition, as-synthesized and in the anhydrous state, in terms of mole ratios, as follows:

| | |
|---|---|
| $SiO_2/Al_2O_3$ | 10 to 55 |
| $Q/SiO_2$ | 0.02 to 0.20 |
| $M/SiO_2$ | 0.01 to 0.20. |

3. The method of claim 1, wherein the zeolite has a composition, as-synthesized and in the anhydrous state, in terms of mole ratios, as follows:

| | |
|---|---|
| $SiO_2/Al_2O_3$ | 15 to 40 |
| $Q/SiO_2$ | 0.05 to 0.20 |
| $M/SiO_2$ | 0.02 to 0.15. |

4. An aluminosilicate LEV framework type zeolite comprising N,N'-dimethyl-1,4-diazabicyclo[2.2.2]octane dications within in its pore structure, wherein the zeolite has a $SiO_2/Al_2O_3$ mole ratio of from 15 to 40.

* * * * *